(12) United States Patent
Utsunomiya et al.

(10) Patent No.: US 8,306,756 B2
(45) Date of Patent: Nov. 6, 2012

(54) METHOD OF DETERMINING BASE SEQUENCE OF NUCLEIC ACID

(75) Inventors: Shinichi Utsunomiya, Kyoto (JP); Makoto Hazama, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 573 days.

(21) Appl. No.: 12/447,253

(22) PCT Filed: Oct. 26, 2006

(86) PCT No.: PCT/JP2006/321353
§ 371 (c)(1),
(2), (4) Date: Apr. 24, 2009

(87) PCT Pub. No.: WO2008/050426
PCT Pub. Date: May 2, 2008

(65) Prior Publication Data
US 2010/0089771 A1    Apr. 15, 2010

(51) Int. Cl.
*G01N 33/48* (2006.01)
(52) U.S. Cl. .......................................................... 702/20
(58) Field of Classification Search ...................... 702/20
See application file for complete search history.

(56) References Cited

U.S. PATENT DOCUMENTS
2002/0090634 A1    7/2002    Hazama

FOREIGN PATENT DOCUMENTS
| JP | 8-173197 A | 7/1996 |
| JP | 2002-202286 A | 7/2002 |
| JP | 2002-228633 A | 8/2002 |
| JP | 2004-527728 A | 9/2004 |
| WO | WO-02/15107 A2 | 2/2002 |
| WO | WO-2004/029298 A2 | 4/2004 |

OTHER PUBLICATIONS

International Search Report for the Application No. PCT/JP2006/321353 mailed Jan. 30, 2007.
Bemo, A.J., "A Graph Theoretic Approach to the Analysis of DNA Sequencing Data", Genome Research, 1996, vol. 6, No. 2, pp. 80-91.
Ewing, Brent et al., "Base-Calling of Automated Sequencer Traces Using Phred.?I. Accuracy? Assessment", Genome Research, 1998, vol. 8, No. 3, pp. 175-185.
Giddings, Michael C. et al., "An Adaptive, Object Oriented Strategy for Base Calling in DNA Sequence Analysis"; Nucleic Acids Research, 1993, vol. 21, No. 19, pp. 4530-4540.
International Preliminary Report on Patentability for Application No. PCT/JP2006/321353 mailed Apr. 28, 2009.

*Primary Examiner* — Jerry Lin
(74) *Attorney, Agent, or Firm* — Cheng Law Group, PLLC

(57) ABSTRACT

To enable accurate analysis of a base sequence even in an electrophoretic pattern containing a degraded part. The base sequence of a nucleic acid is determined by conducting the following steps (A) to (C) in this order: (A) a basic peak extracting step wherein basic peaks are extracted from electrophoretic data involving the respective peaks of the four bases obtained by electrophoresing a sample nucleic acid; (B) a condition determining step wherein a basic peak at the search starting point, from which the search is started, and a standard peak-to-peak distance are determined based on the time-series data composed of the basic peaks extracted above; and (C) a base sequence determining step wherein peak-to-peak intervals are successively scanned forward and backward in the above-described time-series data starting from the basic peak at the search starting point and then the peak-to-peak distance is compared with the standard peak-to-peak distance as determined above so as to add an interpolation peak to a peak-missing area.

8 Claims, 4 Drawing Sheets

METHOD OF DETERMINING BASE SEQUENCE OF NUCLEIC ACID

TECHNICAL FIELD

The present invention relates to a method for determining the base sequence of a nucleic acid such as DNA (deoxyribonucleic acid) from data obtained by measurement using a genetic analyzer utilizing electrophoresis.

BACKGROUND ART

When a genetic analyzer is used to determine the base sequence of DNA, four time-series data sets corresponding to four kinds of bases, A (adenine), G (guanine), C (cytosine), and T (thymine) are obtained.

According to a conventional base sequence determination method such as a method using Phred, prior to peak detection, preprocessing including noise elimination and mobility correction is performed on these time-series data sets. Mobility correction is performed to correct the deviation among the time-series data sets caused by a difference in migration speed among dyes used to label four kinds of bases. Then, peak detection is performed to determine peaks with a large peak height or a large peak area as the peaks of bases (see Non-Patent Document 1).

In measurement using electrophoresis, signal characteristics are widely changed among the initial, middle, and final stages of migration. Based on this fact, one of the present inventors has proposed a noise elimination method in which electrophoretic data is separated into some parts and noise elimination is performed on each of the parts in consideration of such a change in signal characteristics (see Patent Document 1).

Further, when a genetic analyzer is used to detect respective peaks of four kinds of bases in chronological order, there is a case where peak appearance time relatively deviates due to, for example, a difference in migration speed among dyes used to label four kinds of bases. In order to correct the deviation of peak appearance time, one of the present inventors has also proposed a method in which time-series signals are shifted with respect to one another so that the total area of portions where detected peaks overlap each other is minimized (see Patent Document 2).

Non-Patent Document 1: Ewing B, Hillier L, Wendl M, Green P: Base-calling of automated sequencer traces using phred. I. Accuracy assessment. Genome Research 8:175-185, 1998
Patent Document 1: Japanese Patent Application Laid-open No. 2002-202286
Patent Document 2: Japanese Patent Application Laid-open No. 2002-228633

DISCLOSURE OF THE INVENTION

Problem to be Solved by the Invention

In electrophoretic data measured in the final stage of migration, there is a part where it is difficult to detect a peak because its peak shape is unclear due to peak broadening or a small peak is hidden in the foot of a broad peak. Therefore, electrophoretic data measured in the final stage of migration is more likely to lack peak information that is a clue to determining a base sequence, and therefore cannot be accurately analyzed by a conventional base sequence determination method, such as a method using Phred, which depends on only electrophoretic data based on peaks detected by a peak detection operation to determine a base sequence.

In general, in the middle stage of migration, peaks with clear shapes are stably observed at regular intervals, but there is a case where electrophoretic data is partially degraded for a reason resulting from, for example, the reaction state of a measurement object. When data degradation occurs in electrophoretic data, the electrophoretic data cannot be accurately analyzed by a conventional processing method, such as a method using Phred, based on the premise that electrophoretic data to be analyzed is stable, even when it is electrophoretic data measured in the middle stage of migration.

It is an object of the present invention to provide a method capable of accurately determining a base sequence even from electrophoretic data containing a degraded part.

Means for Solving the Problem

The present invention is directed to a method for determining the base sequence of a nucleic acid, including the following steps (A) to (C) in this order: (A) a basic peak extracting step in which basic peaks are extracted from electrophoretic data containing respective peaks of four kinds of bases obtained by electrophoresing a sample nucleic acid; (B) a condition determining step in which a basic peak at search starting point from which a search is started and a standard peak-to-peak distance are determined based on time-series data composed of the extracted basic peaks; and (C) a base sequence determining step in which a search is started from the basic peak at search starting point to sequentially scan intervals between adjacent basic peaks in temporal forward and backward directions in the time-series data and the distance of each interval between adjacent basic peaks is compared with the standard peak-to-peak distance to add an interpolation peak to a peak-missing area to determine a base sequence of the sample nucleic acid.

The basic peak refers to a clear peak of a base. In the basic peak extracting step, basic peaks are extracted, for example, in the following manner. The peak height and/or the peak area of a peak that can be obviously regarded as a peak of a base are/is set as a threshold value(s), and then the peak height and/or the peak area of each peak contained in total time-series data (i.e., electrophoretic data) are/is compared with the threshold value(s) to extract peaks having a peak height or a peak area larger than the threshold value as basic peaks.

Then, after the completion of the condition determining step, the base sequence determining step is performed to add an interpolation peak to a peak-missing area. More specifically, the distance of each interval between adjacent basic peaks is compared with the standard peak-to-peak distance, and then a required number of interpolation peaks are added to a peak-missing area so that a peak-to-peak distance comes close to the standard peak-to-peak distance.

The kind of base of an interpolation peak to be added is determined based on electrophoretic data located at a peak position where the interpolation peak is to be added. A peak located at a position where an interpolation peak is to be added is a signal whose level is too low to be detected as a basic peak.

By providing the step of adding an interpolation peak, it is possible to reproduce, as an interpolation peak, a peak that appears in the final stage of migration but is difficult to detect due to its unclear peak shape or a small peak hidden in the foot of an adjacent broad peak due to its low peak height or small peak area. Further, it is also possible to obtain accurate base sequence information even when peak shape degradation occurs for any reason in part of electrophoretic data, which includes a case where data degradation occurs in the middle stage of migration.

It is preferred that the method for determining a base sequence according to claim 1 further includes the following steps (a) to (c) in this order between the steps (A) and (B): (a) an area dividing step in which time-series data composed of the extracted basic peaks is divided into small areas; (b) a best area extracting step in which the best area showing the best arrangement of basic peaks is extracted from the divided areas; and (c) a mobility correction step in which a mobility correction amount is calculated from the extracted best area based on a difference in mobility among four kinds of bases, and then mobility correction is performed on the total time-series data based on the mobility correction amount, wherein the time-series data having been subjected to mobility correction in the step (c) is used as time-series data in the step (B).

The size of each small area divided in the area dividing step (a) is previously determined so that the distance between adjacent peaks can be regarded as substantially constant in each small area. If the size of each small area is too large, the distance between adjacent peaks varies in each small area, and therefore it is difficult to differentiate between a good area and a bad area. On the other hand, if the size of each small area is too small, the number of peaks contained in each small area is small so that the amount of information usable for a discrimination operation becomes small. For this reason, the size of each small area is preferably determined so that each small area contains, for example, about 100 to 300 bp.

In the best area extracting step (b), the best area is extracted from small areas obtained by dividing the time-series data in the area dividing step. At this time, evaluation of the arrangement of basic peaks is performed on each small area based on the characteristics of electrophoretic data that clear peaks of bases that can be extracted as basic peaks appear more evenly at more regular intervals in the data when migration is more successfully performed. Then, a small area showing the best arrangement of basic peaks is extracted as the best area.

The best area extracting step (b) can be performed by, for example, performing the best mobility correction on each small area based on a difference in mobility among four kinds of bases and then extracting a small area having the largest total peak area as the best area. The best mobility correction can be performed, for example, in the following manner. Four kinds of detection data sets corresponding to four kinds of bases are overlaid together in each small area, and then while one to three kinds of detection data sets out of the four kinds of detection data sets are fixed, the remaining detection data set(s) is(are) shifted in temporal forward and backward directions so that the total area of a peak waveform is maximized.

The best area extracting step (b) can be performed also by, for example, measuring the distances between adjacent basic peaks in each small area and then extracting a small area having the smallest dispersion in distances between adjacent basic peaks as the best area. The dispersion in distances between adjacent basic peaks can be evaluated by, for example, the ratio between a minimum distance between adjacent basic peaks (Dmin) and a maximum distance between adjacent basic peaks (Dmax) in each small area. In this case, a larger ratio of Dmin/Dmax indicates a smaller dispersion in distances between adjacent basic peaks. When it is judged that a small area contains only a repeated sequence, the evaluation of the small area is preferably downgraded by multiplying its ratio of Dmin/Dmax by a value smaller than 1.

In the area dividing step (a), adjacent small areas may be overlapped with each other to increase the number of areas.

In the mobility correction step (c), four kinds of basic peaks corresponding to four kinds of bases are overlaid together in the best area, and then while one to three kinds of basic peaks out of the four kinds of basic peaks are fixed, the remaining basic peaks are shifted in temporal forward and backward directions so that the total area of a peak waveform is maximized to determine a shift amount(s) of one to three kinds of bases. The shift amount(s) of one to three kinds of bases whereby the total area of a peak waveform is maximized is(are) the mobility correction amount(s) of the one to three kinds of bases.

In a case where a mobility correction amount is calculated in the best area extracting step (b), the mobility correction amount may be used in the mobility correction step (c).

The basic peak at search starting point determined in the condition determining step (B) may be a basic peak having the largest peak area in the best area.

The standard peak-to-peak distance determined in the condition determining step (B) may be an average distance between adjacent basic peaks calculated from a part of the best area where basic peaks are spaced at regular intervals.

Effects of the Invention

According to the present invention, basic peaks are first extracted and then an interpolation peak is added to a peak-missing area between adjacent basic peaks, and therefore it is possible to secure reliable information and then pick up less reliable information using the reliable information. Therefore, it is possible to keep a high degree of accuracy in reading base sequence information even in a case where data is partially degraded and therefore peak detection cannot be performed due to signal waveform degradation or a peak is so small that it is hidden in the foot of an adjacent peak, such as a case where data is partially degraded for a reason resulting from, for example, the reaction state of a measurement object.

Further, by performing mobility correction using the mobility correction means based on a mobility correction amount calculated from the best area, it is possible to reduce the occurrence of overtaking or overlapping between the peaks of bases caused by a difference in migration speed among four kinds of bases. Further, by providing the area dividing step, the best area extracting step, and the mobility correction step, it is possible to accurately detect a peak-missing area in the base sequence determining step and properly add an interpolation peak to the peak-missing area, thereby improving the degree of accuracy in determining a base sequence. This makes it possible to more accurately read the information of a longer base sequence from data measured by a genetic analyzer.

Figure 1:
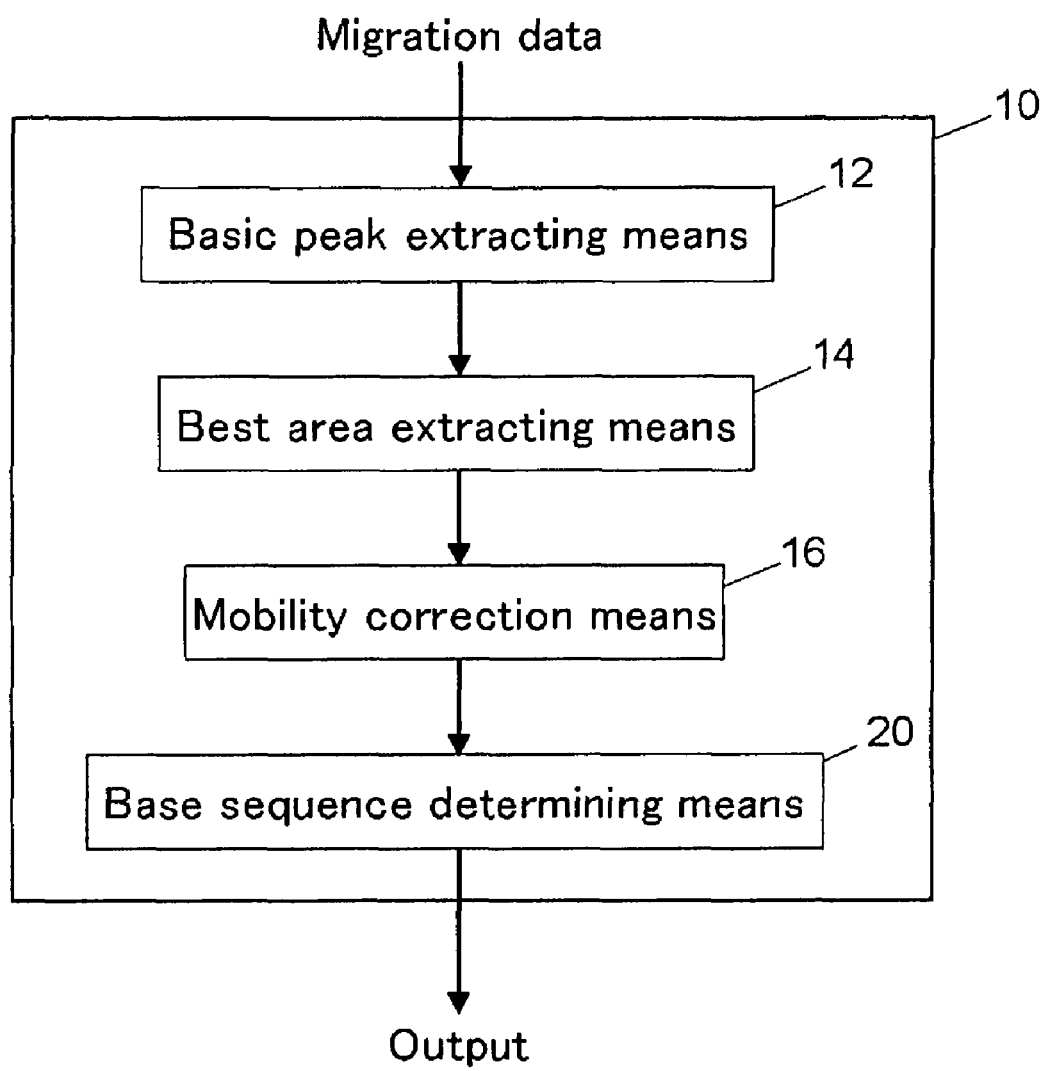
FIG. 1 is a block diagram showing functions for carrying out a method according to one embodiment of the present invention.

DESCRIPTION OF THE REFERENCE NUMERALS 10 computer
12 basic peak extracting means
14 best area extracting means
16 mobility correction means
20 base sequence determining means

DETAILED DESCRIPTION OF THE INVENTION

FIG. 1 is a block diagram showing functions for performing processing steps included in a method according to one embodiment of the present invention. A basic peak extracting means 12 is a function for performing a basic peak extracting step. A best area extracting means 14 is a function for performing an area dividing step and a best area extracting step. A mobility correction means 16 is a function for performing a mobility correction step, and the mobility correction step is performed on total time-series data. A base sequence determining means 20 performs a condition determining step and then a base sequence determining step on the total time-series data incorporated by the mobility correction means 16. In the base sequence determining step, an interpolation peak is added to a peak-missing area.

The basic peak extracting means 12, the best area extracting means 14, the mobility correction means 16, and the base sequence determining means 20 are functions that are achieved by a computer 10. The computer 10 is a computer dedicated to an electrophoresis apparatus or a general-purpose personal computer.

Electrophoretic data is detected by an electrophoresis apparatus and is first stored in a memory device, and is then incorporated into the computer 10 and processed. A base sequence determined by the base sequence determining means 20 is outputted to a recorder or a display, and is then stored in a memory device or sent to another computer.

In a case where it is not necessary to perform mobility correction because a difference in migration speed among dyes used to label four kinds of bases, A, G, C, and T is not so large, the mobility correction step performed by the mobility correction means 16 may be omitted. In this case, after the basic peak extracting step is performed by the basic peak extracting means 12, the base sequence determining step is performed by the base sequence determining means 20 without performing the mobility correction step.

Figure 2:
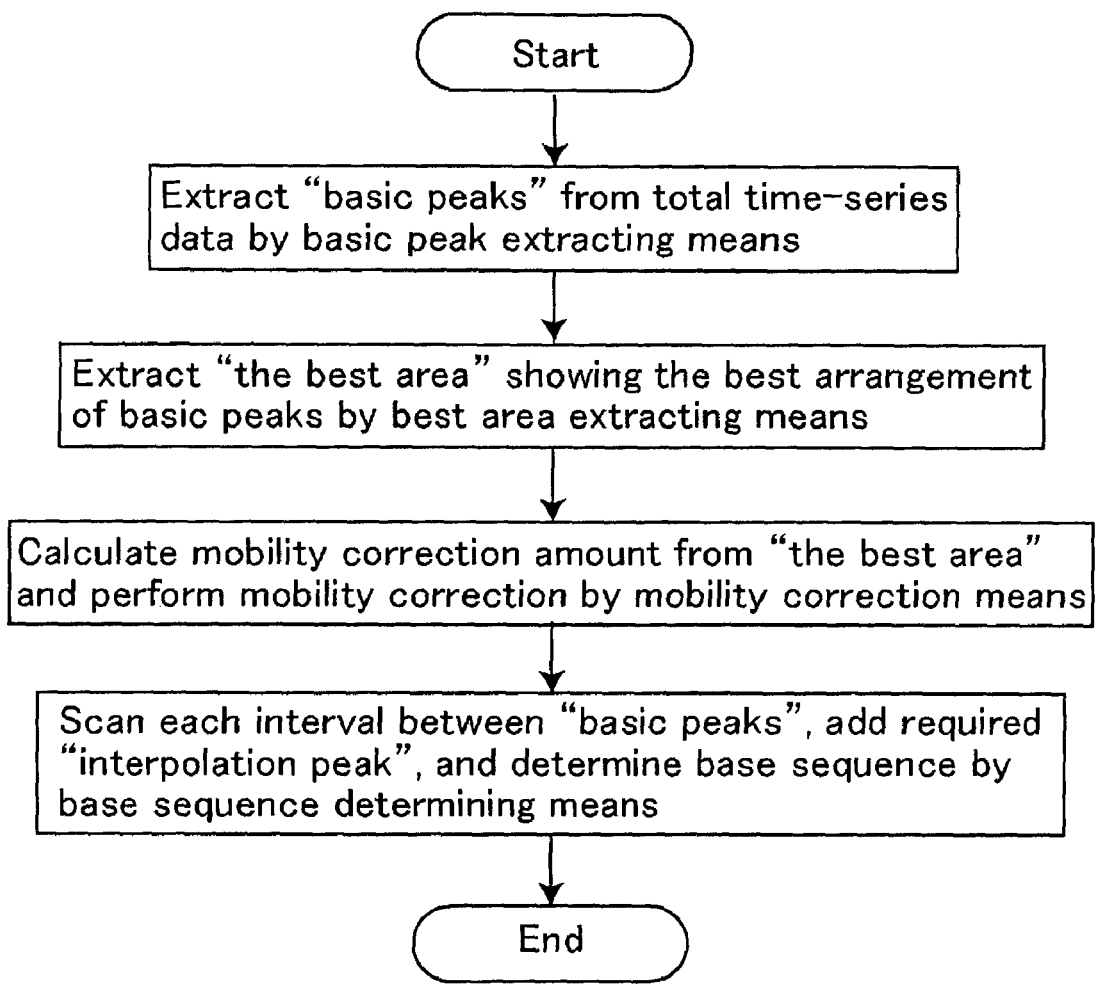
FIG. 2 is a flow chart of the method according to one embodiment of the present invention.
Figure 3:
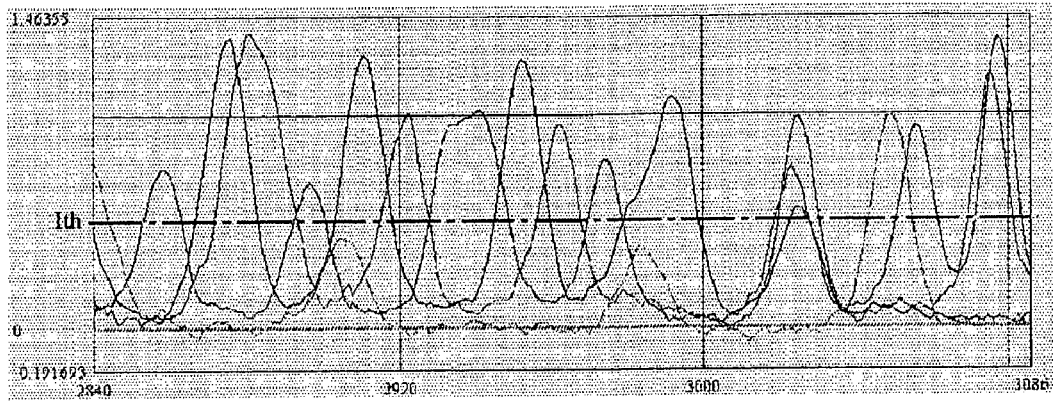
FIG. 3 is a graph showing electrophoretic data of four kinds of bases.

FIG. 2 is a flow chart of the method according to one embodiment of the present invention. FIG. 3 shows examples of signal waveforms obtained as electrophoretic data by electrophoresis measurement performed using dyes for labeling four kinds of bases, A, G, C, and T. In FIG. 3, a horizontal axis represents time, and values plotted on the horizontal axis are the number of scans performed by a detection part of an electrophoresis apparatus using exciting light to detect fluorescence. The number of scans is proportional to time. In FIG. 3, a vertical axis represents the intensity of fluorescence detected at the respective fluorescence wavelengths of the labeling dyes.

The method according to the present embodiment processes electrophoretic data, such as one shown in FIG. 3, in which time-series data sets are temporal deviated with respect to one another due to a difference in migration speed among labeling dyes. Hereinbelow, operations for carrying out the method according to the present embodiment will be described with reference to FIG. 1 which is a block diagram showing functions for carrying out the method and FIG. 2 which is a flow chart of the method.

(Basic Peak Extraction)

First, the basic peak extracting step is performed by the basic peak extracting means 12 on each peak contained in the respective time-series data sets of four kinds of bases shown in FIG. 3 to extract basic peaks, or clear peaks.

In order to extract basic peaks, it is also necessary to perform a peak detection operation. Such a peak detection operation can be performed by a known method generally used. Extraction of basic peaks is performed by, for example, sequentially searching a point, at which the gradient of a measured data signal value is changed from positive to negative, as a candidate for a peak top and then extracting, as basic peaks, only peaks whose signal value at the peak top (i.e., peak height) and/or peak area are/is larger than their respective predetermined threshold values Ith.

In actual measured data, some peaks of bases have a small peak height or unclear peak shape. If a threshold value is set low, noise waveforms as well as such peaks of bases are extracted as basic peaks. Therefore, in this step, a threshold value is set high so that noise waveforms can be reliably eliminated, that is, only the peaks of bases can be reliably extracted as basic peaks.

(Best Area Extraction)

Then, the area dividing step and the best area extracting step are performed by the best area extracting means 14. In the area dividing step, time-series data composed of the extracted basic peaks is divided into small areas. The size of each small area is not particularly limited, but is set so that each small area contains 100 to 300 bp. An area shown in FIG. 3 is a part of one small area, that is, it is smaller than one small area.

The arrangement of basic peaks in each divided small area is evaluated to extract "the best area" showing the best arrangement of basic peaks. In this step, evaluation of arrangement of basic peaks is performed on each small area based on the characteristics of electrophoretic data that when migration is more successfully performed, basic peaks appear more evenly at more regular intervals in the data.

The evaluation of arrangement of basic peaks can be performed by, for example, a method based on the findings that the best mobility correction amount is a shift amount whereby the total area of a peak waveform is maximized (see Patent Document 2). According to this method, the evaluation value of each small area is a total peak area calculated after the best mobility correction is performed. Therefore, a small area having the largest total peak area is extracted as the best area. More specifically, four kinds of detection data sets corresponding to four kinds of bases are overlaid together in each small area, and then while one to three kinds of detection data sets out of the four kinds of detection data sets are fixed, the remaining detection data set(s) is(are) shifted in temporal forward and backward directions so that the total area of a peak waveform is maximized. In this way, the best mobility correction is performed on each small area. Then, a small area whose total area of a peak waveform calculated after the best mobility correction is performed is largest is selected as the best area.

Figure 6A:
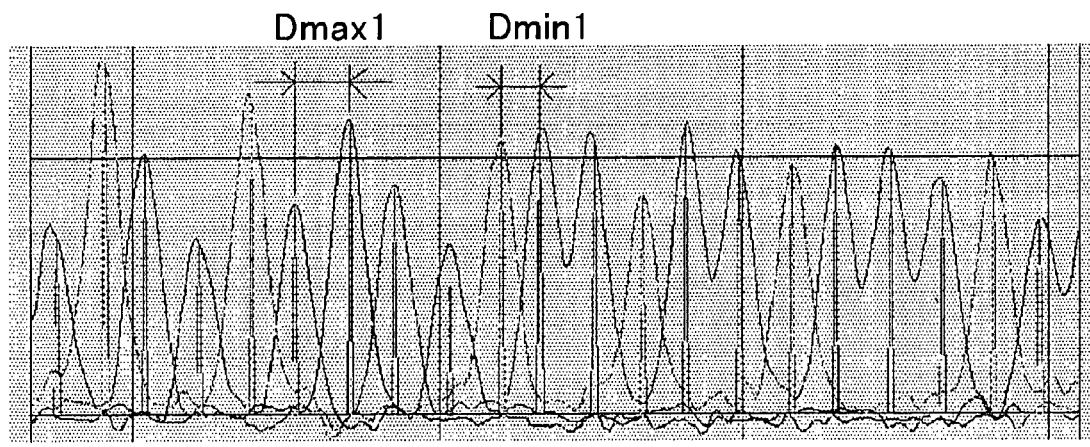
FIG. 6A is a graph showing electrophoretic data in which basic peaks are spaced at substantially regular intervals.
Figure 6B:
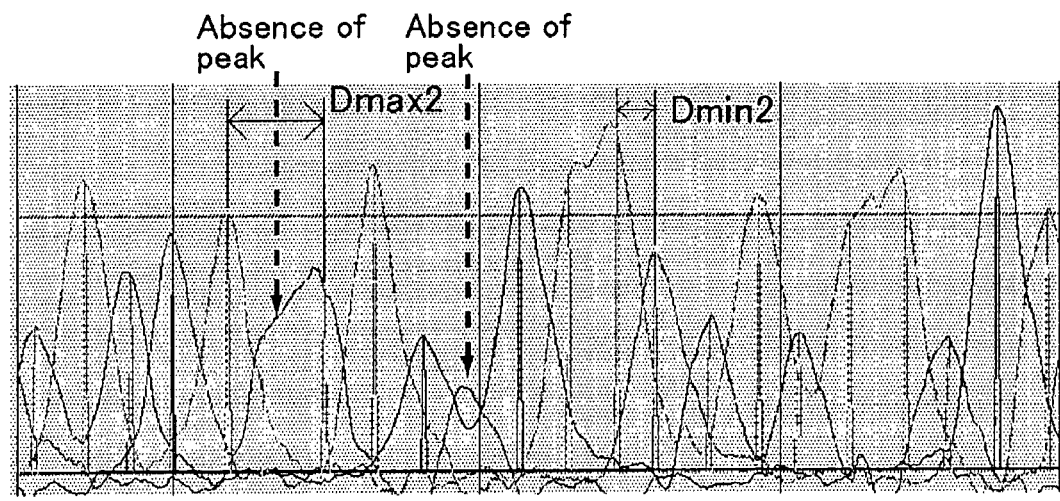
FIG. 6B is a graph showing electrophoretic data in which basic peaks are spaced at irregular intervals.

The evaluation of each small area can be performed also by another method in which distances between adjacent basic peaks are measured in each small area and the dispersion in distances between adjacent basic peaks is evaluated to extract a small area having the smallest dispersion in distances between adjacent basic peaks as the best area. FIGS. 6(A) and 6(B) are graphs showing examples of small areas different in the dispersion in the distances between adjacent basic peaks.

More specifically, FIG. 6(A) is a graph showing an example of a small area in which basic peaks are spaced at substantially regular intervals, and FIG. 6(B) is a graph showing an example of a small area in which basic peaks are spaced at irregular intervals because some peaks of bases have not been detected as basic peaks due to their unclear peak shape or low peak height. These two examples are greatly different in the dispersion in distances between adjacent basic peaks. The dispersion in distances between adjacent basic peaks is evaluated by, for example, utilizing the ratio between a minimum distance between adjacent basic peaks (Dmin) and a maximum distance between adjacent basic peaks (Dmax) in each small area. More specifically, when the value of Dmin/Dmax is larger, the dispersion in distances between adjacent basic peaks is smaller, and on the other hand, when the value of Dmin/Dmax is smaller, the dispersion in distances between adjacent basic peaks is larger. In FIGS. 6(A) and 6(B), the value of Dmin1/Dmax1 is larger than the value of Dmin2/Dmax2, and therefore it can be judged that the dispersion in distances between adjacent basic peaks is smaller in FIG. 6(A) than in FIG. 6(B).

By evaluating all the small areas k=1, 2, ... N using the following formula (1) for determining an evaluation value in such a manner as described above to detect a small area kb having the largest evaluation value, it is possible to select a small area having the smallest dispersion in distances between adjacent basic peaks as "the best area".

$$\text{Evaluation } (k) = D\min(k)/D\max(k) \qquad (1)$$

In general, one of the difficult problems common to base sequence determination methods is that accurate mobility correction cannot be performed when an analysis object is a gene sequence called "repeated sequence" in which only a certain kind(s) of bases selected from four kinds of bases A, G, C, and T are continuously arranged. In the case of using the above-described evaluation method in which the dispersion in distances between adjacent basic peaks of each small area is determined to extract the best area, it is preferred that the evaluation of a small area containing only a "repeated sequence" is downgraded. Whether or not a small area contains only a "repeated sequence" can be determined by checking how many kinds of bases are contained in the small area. When it is judged that the small area contains only a "repeated sequence", the evaluation of the small area is downgraded by, for example, multiplying the evaluation value of the small area obtained by the above formula (1) by a value smaller than 1, for example, 0.5 to select the best area from small areas other than the small area containing only a "repeated sequence".

When the time-series data is divided into small areas, adjacent small areas may be overlapped with each other to increase the number of areas.

In this way, a small area containing basic peaks of four kinds of bases and exhibiting a small dispersion in distances between adjacent basic peaks is extracted as the best area.

(Mobility Correction)

Then, a mobility correction amount is calculated by the mobility correction means 16 from "the best area" extracted in such a manner as described above. Mobility correction is performed, for example, in the following manner. A signal string composed of the basic peaks of, for example, a base G is fixed, and then a signal string composed of the basic peaks of a base A, a signal string composed of the basic peaks of a base C, and a signal string composed of the basic peaks of a base T are shifted along the temporal axis, wherein the shift amounts of these signal strings are defined as $\Delta A(i)$, $\Delta C(j)$, and $\Delta T(k)$, respectively.

$\Delta A(i) = 0, \pm 1, \pm 2,$ (wherein $i = 1, 2, 3, \ldots$)

$\Delta C(j) = 0, \pm 1, \pm 2,$ (wherein $j = 1, 2, 3, \ldots$)

$\Delta T(k) = 0, \pm 1, \pm 2,$ (wherein $k = 1, 2, 3, \ldots$)

The total area S (i, j, k) of basic peaks contained in the best area is determined for each combination of the shift amounts $\Delta A(i)$, $\Delta C(j)$, and $\Delta T(k)$. The shift amounts $\Delta A(ib)$, $\Delta C(jb)$, and $\Delta T(kb)$, the combination of which makes the total area S (i, j, k) maximum, are the mobility correction amounts of bases A, C, and T, respectively.

It is to be noted that when a mobility correction amount is calculated to extract "the best area" in the best area extracting step, the mobility correction amount can be used in the mobility correction step.

The mobility correction amount(s) is(are) applied to the total data to perform mobility correction.

(Addition of Interpolation Peak)

Figure 4:
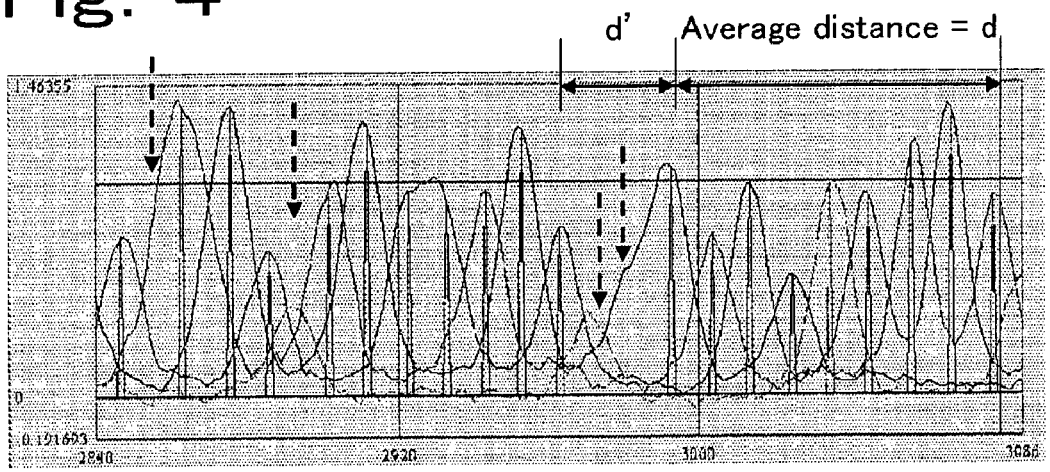
FIG. 4 is a graph showing electrophoretic data obtained by performing mobility correction.

FIG. 4 is a graph showing electrophoretic data obtained by performing mobility correction on signal strings shown in FIG. 3. As shown in FIG. 4, the deviation among the time-series data sets is corrected by mobility correction so that overlapping or overtaking between peaks is eliminated. As a result, all the peaks are spaced at substantially regular intervals. In FIG. 4, impulse signals indicate peak detection positions. However, the basic peaks do not include all the peaks of bases, and some peaks of bases indicated by dashed arrows in FIG. 4 are missed.

Therefore, the base sequence determining means 20 is operated to detect these missing peaks of bases and add interpolation peaks. Here, a basic peak at search starting point and a standard peak-to-peak distance are determined, and then a search is started from the basic peak at search starting point to sequentially scan intervals between adjacent basic peaks in temporal forward and backward directions and a required number of interpolation peaks are added to a peak-missing area.

The basic peak at search starting point is determined so as to satisfy the requirement that, for example, its peak area is largest in "the best area".

The standard peak-to-peak distance is determined by, for example, calculating an average peak-to-peak distance from a part of the best area where basic peaks are spaced at regular intervals. Further, the standard peak-to-peak distance may be monotonously and gradually decreased during sequential scanning in temporal forward and backward directions based on the characteristics of electrophoresis that a peak-to-peak distance is gradually decreased from the middle stage to the initial stage of migration and from the middle stage to the final stage of migration. Alternatively, the standard peak-to-peak distance may be gradually changed from area to area. In this case, the average peak-to-peak distance of an area, on which searching of a peak-missing area and addition of an interpolation peak have already been performed, is used as the standard peak-to-peak distance of the next area.

A method for searching a peak-missing area and adding an interpolation peak will be described below with reference to FIG. 4. The average peak-to-peak distance d of a part located on the right side of an area shown in FIG. 4 (i.e., a part on the side where the base pair number is larger) where peaks are extracted at substantially regular intervals is determined, and the average peak-to-peak distance d is defined as a standard peak-to-peak distance. The peak-to-peak distance of the next part is expected to be close to d, but is actually d' as shown in FIG. 4. In this case, a new peak-to-peak distance NewD(n) can be expressed by the following formula (2) assuming that n interpolation peaks are added to this area.

New $D(n)=d'/(n+1)$ (2)

wherein n=0, 1, or 2

Then, n is determined so that a new peak-to-peak distance NewD(n) becomes closest to the standard peak-to-peak distance d, and the thus determined n is defined as the number of interpolation peaks that should be added. The added interpolation peaks are detected at positions spaced apart by a distance NewD(n).

The kind of base of an interpolation peak to be added is determined in the following manner. In the case of the above example, assumed time centers to which interpolation peaks are to be added so that basic peaks located at both ends of a peak-to-peak interval having a distance d' and the interpolation peaks are spaced at regular intervals are determined. Then, the threshold value is lowered at around each assumed time center to detect a peak. When a peak is detected, the kind of base of the peak is determined as the kind of base of an interpolation peak to be added. On the other hand, when it is difficult to detect a peak due to its unclear peak shape, the kind of base of time-series data having the highest signal value is selected as the kind of base of an interpolation peak to be added. As a result of addition of interpolation peaks, a peak sequence as shown in FIG. 5 is finally obtained.

(Base Sequence Determination)

Figure 5:
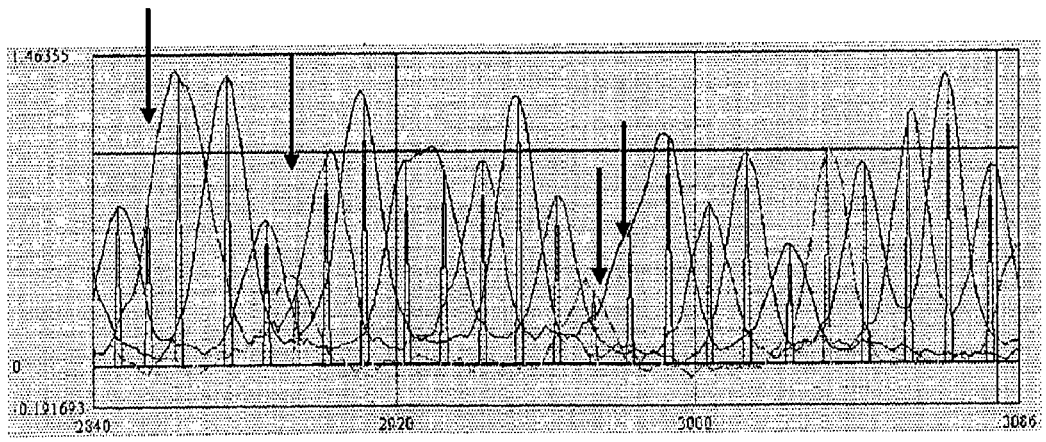
FIG. 5 is a graph showing electrophoretic data obtained by further adding interpolation peaks to the electrophoretic data shown in FIG. 4.

A base sequence can be determined by sequentially reading a peak sequence such as one shown in FIG. 5.

According to the present embodiment, since the best area is extracted by processing based on only basic peaks believed to give reliable information in the early stage of the method, and then mobility correction is performed based on a mobility correction amount calculated from the best area, disturbance caused by less reliable information is less likely to occur even when data having a degraded part is processed. Therefore, the method according to the present embodiment is less likely to be influenced by partial change in electrophoretic data such as data quality degradation, and therefore can determine a base sequence with stability.

INDUSTRIAL APPLICABILITY

The present invention can be applied to determination of a base sequence from measured data obtained by electrophresing a nucleic acid such as DNA or RNA.

What is claimed is:

1. A method for determining a base sequence of a nucleic acid, comprising the following steps (A) to (C) in this order:
   (A) a basic peak extracting step in which basic peaks are extracted from electrophoretic data containing respective peaks of four kinds of bases obtained by electrophoresing a sample nucleic acid, the basic peaks being peaks having a peak height or a peak area larger than a threshold value;
   (B) a condition determining step in which a basic peak at a search starting point from which a search is started and a standard peak-to-peak distance are determined based on time-series data composed of the extracted basic peaks; and
   (C) a base sequence determining step in which a search is started from the basic peak at a search starting point to sequentially scan intervals between adjacent basic peaks in temporal forward and backward directions in the time-series data, and then a distance of each interval between adjacent basic peaks is compared with the standard peak-to-peak distance to add an interpolation peak to a peak-missing area to determine a base sequence of the sample nucleic acid, wherein the method further comprises the following steps (a) to (c) in this order between the Steps (A) and (B):
   (a) an area dividing step in which time-series data composed of the extracted basic peaks is divided into small areas;
   (b) a best area extracting step in which a best area showing a best arrangement of basic peaks is extracted from the divided areas; and
   (c) a mobility correcting step in which a mobility correction amount is calculated from the extracted best area based on a difference in mobility among four kinds of bases, and then mobility correction is performed on the total time-series data based on the mobility correction amount, wherein the time-series data having been subjected to mobility correction in the step (c) is used as time-series data in the step (B), and
   wherein in the best area extracting step (b), distances between adjacent basic peaks are measured in each small area, and an area having a smallest dispersion in distances between adjacent basic peaks is extracted as the best area, and
   wherein the steps (A)-(C) and (a)-(c) are performed by a data processing computer.

2. The method for determining a base sequence according to claim 1, wherein the dispersion in distances between adjacent basic peaks is evaluated by a ratio between a minimum distance between adjacent basic peaks Dmin and a maximum distance between adjacent basic peaks Dmax in each small area, and wherein when the ratio of Dmin/Dmax is larger, the dispersion in distances between adjacent basic peaks is smaller.

3. The method for determining a base sequence according to claim 2, wherein when it is determined that a small area contains only a repeated sequence, the evaluation of the small area is downgraded by multiplying the ratio of Dmin/Dmax of the small area by a value smaller than 1.

4. The method for determining a base sequence according to claim 1, wherein in the area dividing step (a), adjacent small areas are overlapped with each other to increase the number of areas.

5. The method for determining a base sequence according to claim 1, wherein in the mobility correction step (c), four kinds of basic peaks corresponding to four kinds of bases are overlaid together in the best area, and then while one to three kinds of basic peaks out of the four kinds of basic peaks are fixed, remaining basic peaks are shifted in temporal forward and backward directions so that a total area of a peak waveform is maximized to determine a shift amount(s) of one to three kinds of bases, and wherein the shift amount(s) of one to three kinds of bases whereby a total area of a peak waveform is maximized is(are) defined as a mobility correction amount (s) of the one to three kinds of bases.

6. The method for determining a base sequence according to claim 1, wherein the basic peak at search starting point determined in the condition determining step (B) is a peak having a largest peak area in the best area.

7. The method for determining a base sequence according to claim 1, wherein the standard peak-to-peak distance determined in the condition determining step (B) is an average peak-to-peak distance calculated from a part of the best area where basic peaks are spaced at regular intervals.

8. The method for determining a base sequence according to claim 1,
   wherein the data processing computer has a basic peak extracting means, a best area extracting means, a mobility correction means, and a base sequence determining means as functions achieved by the computer, wherein the basic peak extracting means performs the basic peak extracting step, the best area extracting means performs the area dividing step and the best area extracting step, the mobility correction means performs the mobility correction step on total time-series data, and the base sequence determining means performs the condition determining step and then the base sequence determining step on the total time-series data incorporated by the mobility correction means, and wherein the data processing computer outputs the base sequence determined by the base sequence determining means.

\* \* \* \* \*